(12) United States Patent
Huang

(10) Patent No.: US 10,070,820 B2
(45) Date of Patent: *Sep. 11, 2018

(54) TRANSDERMAL MICRONEEDLE CONTINUOUS MONITORING SYSTEM

(71) Applicant: Micro Nipple Technology Co., Ltd., Taipei (TW)

(72) Inventor: Juang-Tang Huang, Taipei (TW)

(73) Assignee: Micro Nipple Technology Co., Ltd., Taipei (TW)

( * ) Notice: Subject to any disclaimer, the term of this patent is extended or adjusted under 35 U.S.C. 154(b) by 1131 days.

This patent is subject to a terminal disclaimer.

(21) Appl. No.: 14/265,234

(22) Filed: Apr. 29, 2014

(65) Prior Publication Data

US 2015/0208984 A1 Jul. 30, 2015

(30) Foreign Application Priority Data

Jan. 28, 2014 (TW) .............................. 103103314 A

(51) Int. Cl.
| | |
|---|---|
| *A61B 5/00* | (2006.01) |
| *A61B 5/15* | (2006.01) |
| *A61B 5/05* | (2006.01) |
| *A61B 5/145* | (2006.01) |

(52) U.S. Cl.
CPC ................ *A61B 5/685* (2013.01); *A61B 5/05* (2013.01); *A61B 5/150022* (2013.01); *A61B 5/150282* (2013.01); *A61B 5/150984* (2013.01); *A61B 5/6849* (2013.01); *A61B 5/14514* (2013.01); *A61B 5/14532* (2013.01); *A61B 5/6833* (2013.01); *A61B 2562/046* (2013.01); *A61B 2562/125* (2013.01)

(58) Field of Classification Search
CPC .............. A61B 5/685; A61B 5/150282; A61B 5/150022; A61B 5/6849; A61B 5/05; A61B 5/150984; A61B 5/14514; A61B 2562/046; A61B 2562/125; A61B 5/14532; A61B 5/6833
See application file for complete search history.

(56) References Cited

U.S. PATENT DOCUMENTS

| | | | | |
|---|---|---|---|---|
| 6,565,532 | B1 * | 5/2003 | Yuzhakov | A45D 34/04 604/142 |
| 7,344,499 | B1 | 3/2008 | Prausnitz et al. | |
| 2006/0036209 | A1 * | 2/2006 | Subramony | A61M 37/0015 604/20 |

FOREIGN PATENT DOCUMENTS

WO WO 2008/100118 * 8/2008

* cited by examiner

*Primary Examiner* — Tiffany Weston
(74) *Attorney, Agent, or Firm* — Parker Ibrahim & Berg LLC; James M. Behmke; Stephen D. LeBarron

(57) ABSTRACT

Transdermal microneedles continuous monitoring system is provided. The continuous system monitoring includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the edge. One of the sheets provides the through hole from which the barbules at the edge of the other sheets go through, and the barbules are disposed separately.

11 Claims, 10 Drawing Sheets

TRANSDERMAL MICRONEEDLE CONTINUOUS MONITORING SYSTEM

BACKGROUND OF THE INVENTION

Field of the Invention

The present invention relates to a transdermal sensor, especially to a transdermal sensor obtain physiologic data by measuring the concentration of hypodermal target molecules.

Description of the Related Art

Tissue fluid is mainly contained in subcutaneous tissue and includes amino acids, sugars, fatty acids, coenzymes, hormones, neurotransmitters, salts and waste products from the cells. Moreover, the tissue fluid is also the major communication channel for cell and blood. The concentrations of the various components in the tissue fluid are useful for determining user's physiological conditions.

The medicine will be slowly released over a long period in tissue fluid when the patient takes or injects the medicine. The concentration variation of medicine in the tissue fluid is continually monitored during development of medicine and clinical experiment. Therefore, the tissue fluid is commonly sampled to further examine or analyze in medical treatment of patient.

The commercially available physiological examination instruments generally withdraw tissue fluid by using a needle piercing through stratum corneum. However, the patient may feel painful for this kind of invasive sampling way. Moreover, the patient may be infected by microorganism originally present on epidermis and entering the patient body as the stratum corneum is pierced by a needle. Transdermal sensor with array-arranged microneedles pricking through skin is developed to withdraw tissue fluid in painless and minimally-invasive way.

The array-arranged microneedles of a transdermal sensor can be manufactured with standard semiconductor process such as photolithograph process and etching process. U.S. Pat. No. 7,344,499 discloses a process for manufacturing silicon microneedles. As can be seen from the second paragraph of the twelve column of this patent, firstly a silicon wafer with a first patterned photoresist layer is prepared. Next, a through hole is defined on the wafer by anisotropic etching. Afterward, a chromium layer is coated on the wafer and a second patterned photoresist layer is formed atop the through hole to function as circular etching mask. Next, the wafer is then etched to form outer tapered wall for the microneedles. However, the silicon-based microneedles are brittle and tend to break when the microneedles prick through user's skin.

Alternatively, hollow microneedles with resin barbules are proposed, where the barbules are drilled by laser processing. Firstly, sheet with barbules is formed by extruding polyimide or polyether ether ketone, and then the barbules are drilled by laser to form hollow microneedles. However, the microneedles have compact size such that the barbules may have ragged edge after extrusion. Moreover, it is difficult to form a hollow microneedle with off-axis through hole or central through hole having uniform inner diameter by laser processing.

SUMMARY OF THE INVENTION

One object of the present invention is to provide a transdermal microneedles continuous monitoring system, where the monitoring system has microneedles made by punching or etching to have sufficient mechanical strength. The microneedle can be kept intact after the microneedle pricks user's skin for sensing. The microneedle has such structure that the sensing polymer can be advantageously coated on inner surface of the tip of the microneedle. The sensing polymer can be prevented from falling as the microneedle pricks user's skin for sensing.

Accordingly, the present invention provides a transdermal microneedles continuous monitoring system is provided. The transdermal microneedle continuous monitoring system includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the peripheral. One of the sheets provides the through hole from which the barbules at the edge of the other sheets go through, and the barbules are disposed separately.

Another object of the present invention is to provide a sensing device for interstitial fluid, where the sensing device has microneedle made by punching or etching to have sufficient mechanical strength. The microneedle can be kept intact after the microneedle pricks user skin for sensing. The microneedle has such structure that the sensing polymer can be advantageously coated on inner surface of the tip of the microneedle. The sensing polymer can be prevented from falling as the microneedle pricks user's skin for sensing.

Accordingly, the present invention provides a sensing device for interstitial fluid. The sensing device includes a substrate and a microneedle unit. The microneedle unit at least comprises a first microneedle set used as a working electrode and arranged on the substrate in an array, and a second microneedle set used as a reference electrode. The second microneedle set comprises at least a microneedle. The first microneedle set comprises at least a sheet having a through hole on which a barbule forms at the peripheral. One of the sheets provides the through hole from which the barbules at the edge of the other sheets go through, and the barbules are disposed separately.

The microneedle of the present invention has sufficient mechanical strength. The microneedle can be kept intact after the microneedle pricks user skin for sensing. Moreover, the microneedle has simple manufacture process, which is beneficial for mass production.

DETAILED DESCRIPTION OF THE INVENTION

Figure 1:
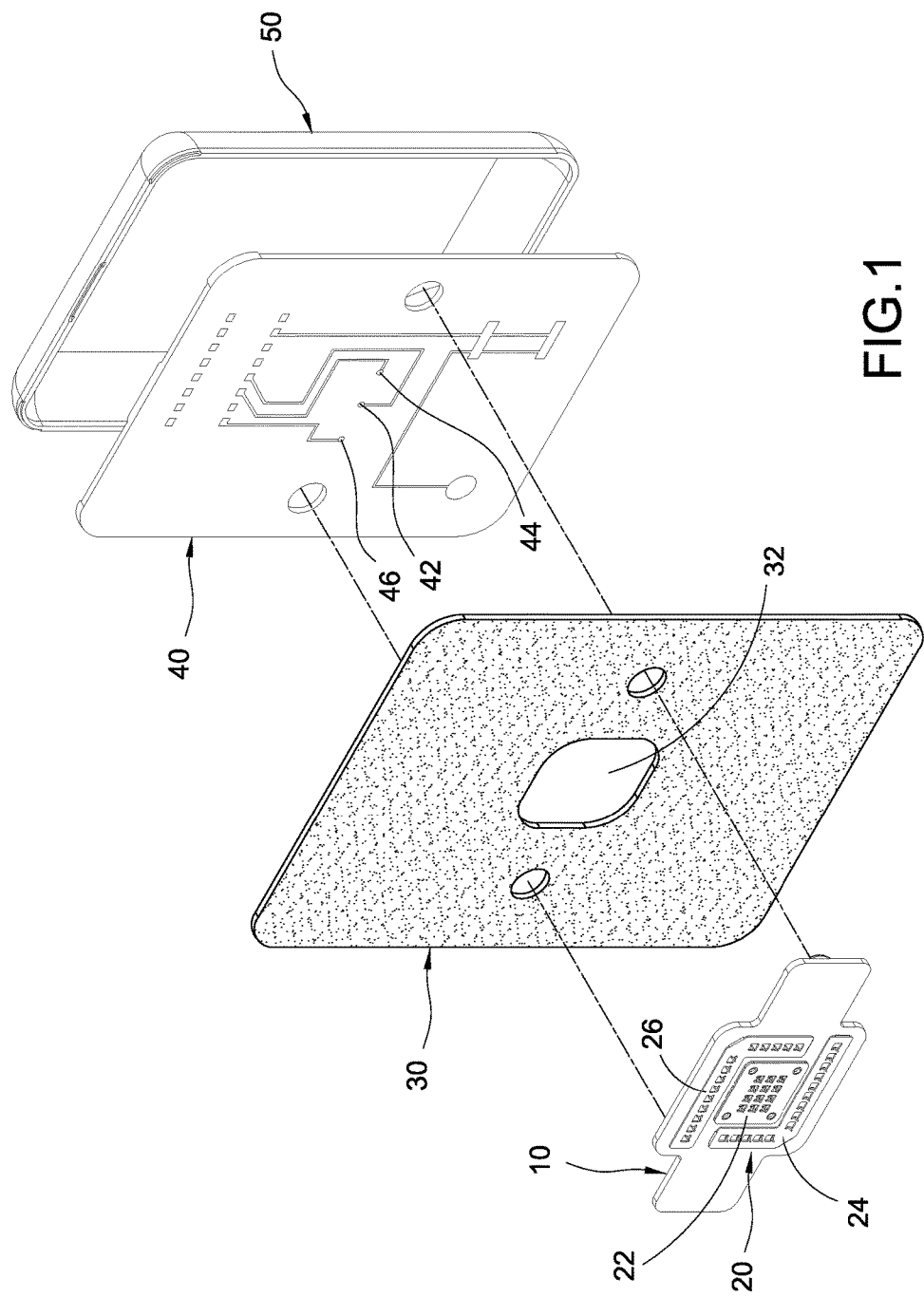
FIG. 1 shows the exploded view of the transdermal microneedles continuous monitoring system according to an embodiment of the present invention from one viewing direction.
Figure 2:
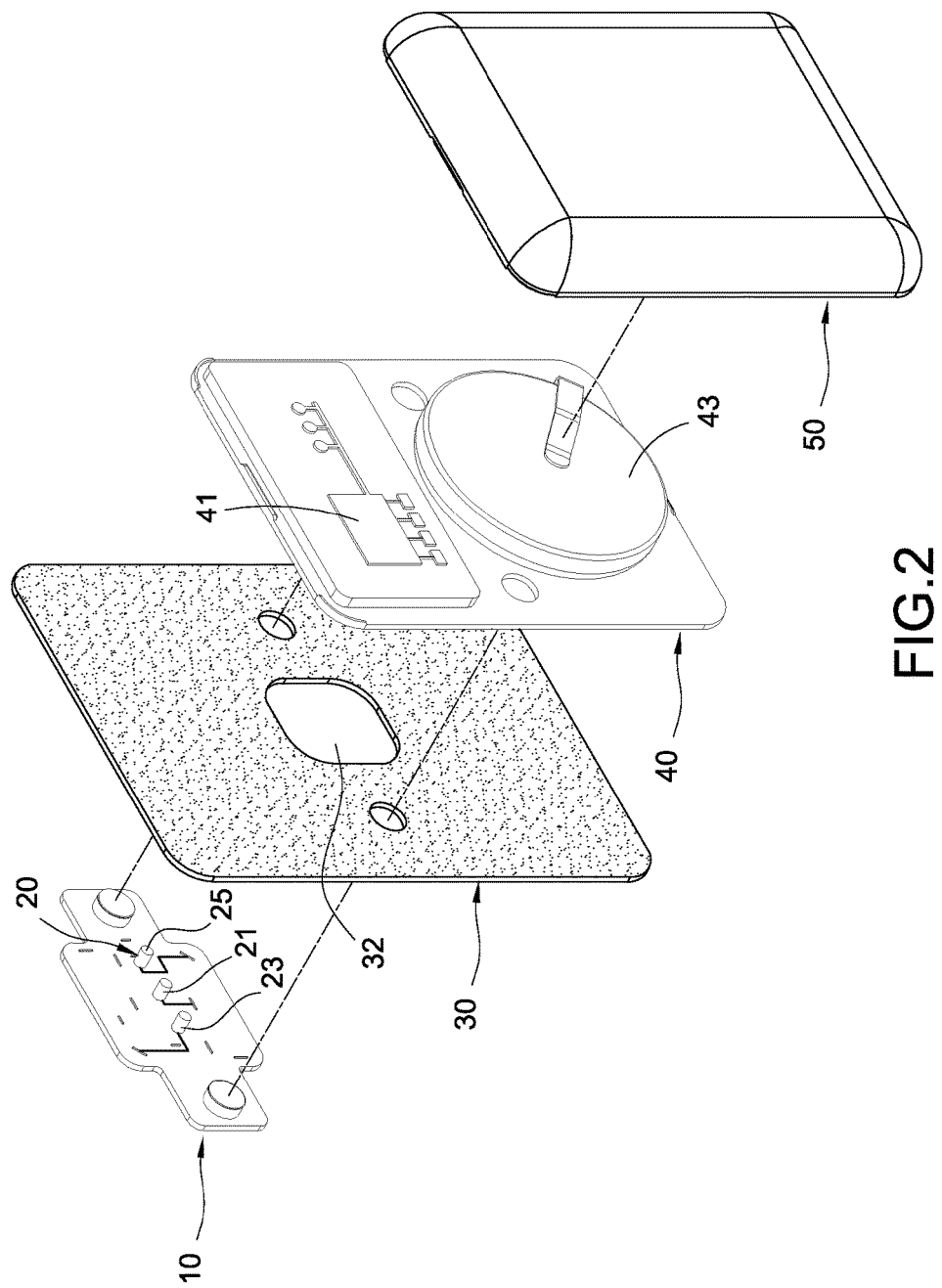
FIG. 2 shows the exploded view of the transdermal microneedles continuous monitoring system from another viewing direction.

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

FIG. 1 shows the exploded view of the transdermal microneedles continuous monitoring system according to an embodiment of the present invention from one viewing direction, and FIG. 2 shows the exploded view of the transdermal microneedles continuous monitoring system from another viewing direction. The transdermal microneedles continuous monitoring system of the present invention mainly comprises a substrate 10, a microneedle unit 20, a flexible pad 30, a signal processing unit 41, a power supply unit 43 and a cover 50, where the signal processing unit 41 and the power supply unit 43 are arranged on a circuit board 40.

According to an embodiment of the present invention, the microneedle unit 20 comprises a first microneedle set 22 used as a working electrode, a second microneedle set 24 used as a reference electrode, and a third microneedle set 26 used as a counter electrode. The flexible pad 30 has an opening 32 through which the microneedle unit 20 passes. The microneedle unit 20 further comprises electric conducting posts 21, 23, 25 to respectively and electrically connect to the contacts 42, 44 and 46 on the circuit board 40. The transdermal microneedles continuous monitoring system of the present invention uses the flexible pad 30 to have tight fit with the user's muscle during operating thereof.

The signal processing unit 41 electrically connects to the microneedle unit 20 and receives a concentration data of hypodermal target molecules sensed by the microneedle unit 20. The signal processing unit 41 generates a sensing signal manifesting the current physiological condition of user after processing the received concentration data. The power supply unit 43 provides working power to the transdermal microneedles continuous monitoring system of the present invention.

Figure 3:
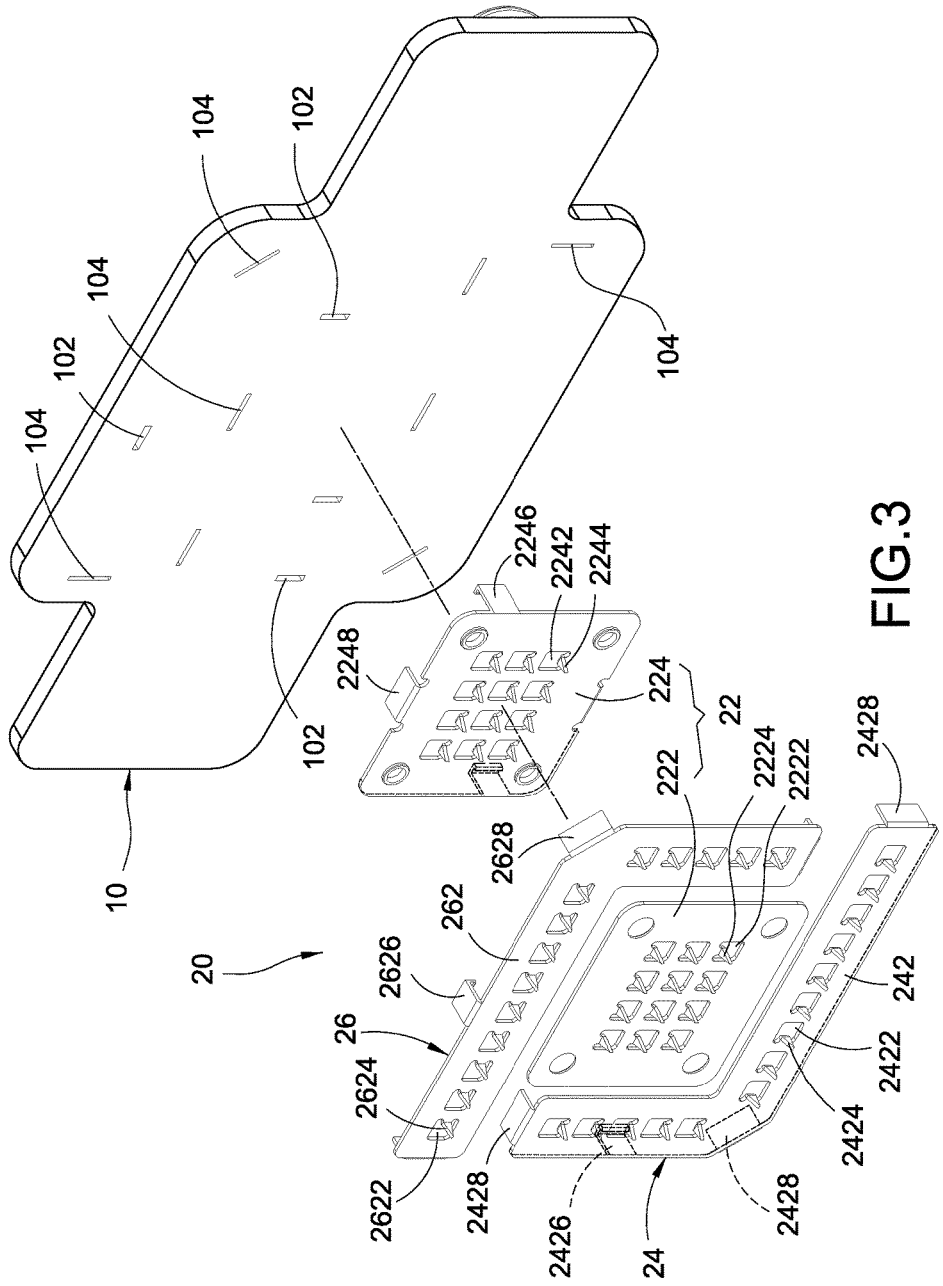
FIG. 3 shows a schematic exploded view of the microneedle unit according to an embodiment of the present invention.

FIG. 3 shows a schematic exploded view of the microneedle unit 20 according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224. The second sheet 224 of the first microneedle set 22 comprises barb 2246 at the peripheral thereof and matched with the aperture 102 defined on the substrate 10. According to another embodiment, the second sheet 224 of the first microneedle set 22 comprises conductive pin 2248 at the peripheral thereof. The conductive pin 2248 can be inserted into a slot 104 defined on the substrate 10 to electrically connect to the conductive post 21.

Similarly, the second microneedle set 24 comprises a first sheet 242. The first sheet 242 has at least one first through hole 2422 defined thereon, and a first barbule 2424 at peripheral of the first through hole 2422. The first sheet 242 of the second microneedle set 24 comprises barb 2426 at the peripheral thereof and matched with the aperture 102 defined on the substrate 10. According to another embodiment, the first sheet 242 of the second microneedle set 24 comprises conductive pin 2428 at the peripheral thereof. The conductive pin 2428 can be inserted into a slot 104 defined on the substrate 10 to electrically connect to the conductive post 23.

Similarly, the third microneedle set 26 also comprises a first sheet 262. The first sheet 262 has at least one first through hole 2622 defined thereon, and a first barbule 2624 at peripheral of the first through hole 2622. The first sheet 262 of the third microneedle set 26 comprises barb 2626 at the peripheral thereof and matched with the aperture 102 defined on the substrate 10. According to another embodiment, the first sheet 262 of the third microneedle set 26 comprises conductive pin 2628 at the peripheral thereof. The conductive pin 2628 can be inserted into a slot 104 defined on the substrate 10 to electrically connect to the conductive post 25.

According to an embodiment of the present invention, the first microneedle set 22, the second microneedle set 24, and the third microneedle set 26 can be made by punching or etching process. The material of the barbules is selected from the group consisting of stainless steel, nickel, nickel alloy, titanium, titanium alloy, carbon nanotube, and silicon. The surface of the barbules is coated with biologically compatible metal. The material of the barbules can also be selected from the group consisting of polycarbonate, polymethacrylic acid, polytetrafluoroethylene, and polyester. The surface of the barbules is also coated with biologically compatible metal. Moreover, the height of the barbules is 300-600 micrometers; the base width of the barbules is 150-450 micrometers. The separation between tips of the barbules is 500-3000 micrometers.

With reference to FIGS. 4 to 7, FIG. 4 is a top view of the microneedle set functioning as working electrode according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224.

Figure 5:
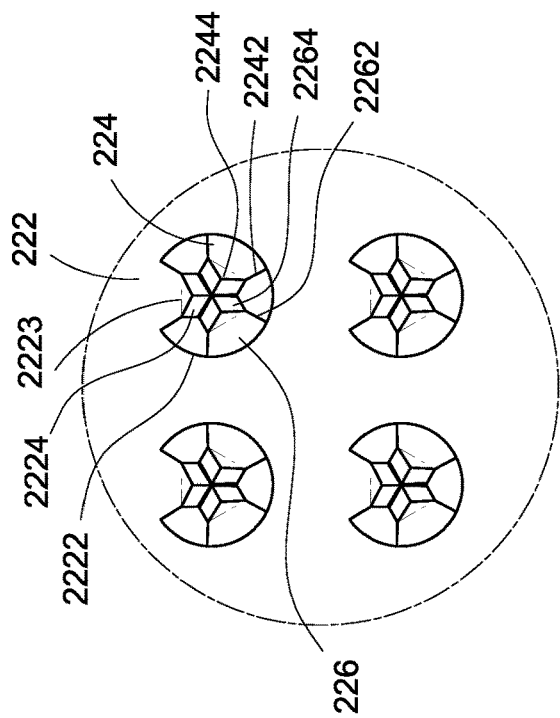
FIG. 5 is a top view of the microneedle set functioning as working electrode according to another embodiment of the present invention.
Figure 4:
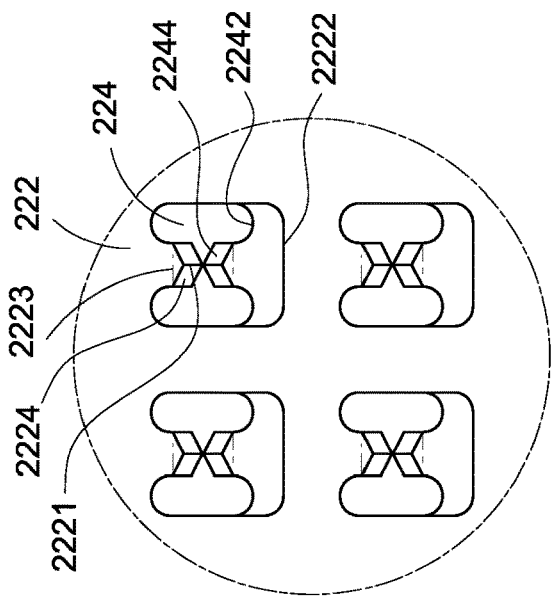
FIG. 4 is a top view of the microneedle set functioning as working electrode according to an embodiment of the present invention.

FIG. 5 is a top view of the microneedle set functioning as working electrode according to another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in right triangular arrangement from top view.

Figure 6:
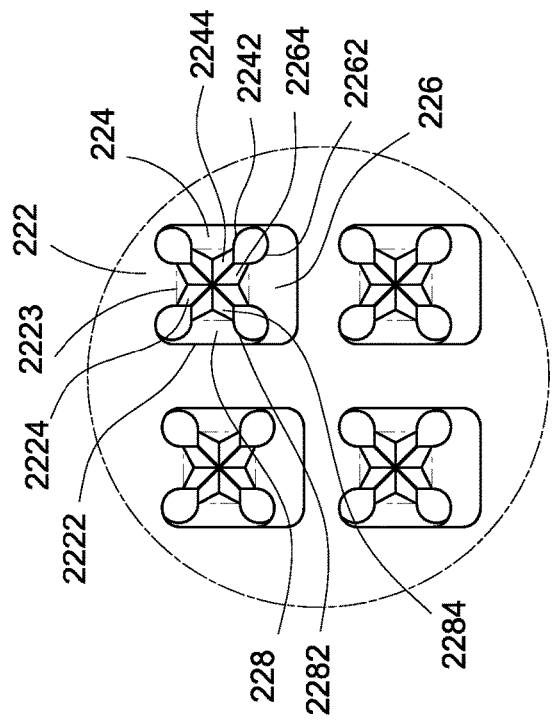
FIG. 6 is a top view of the microneedle set functioning as working electrode according to still another embodiment of the present invention.

FIG. 6 is a top view of the microneedle set functioning as working electrode according to still another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in isosceles triangular arrangement from top view.

Figure 7:
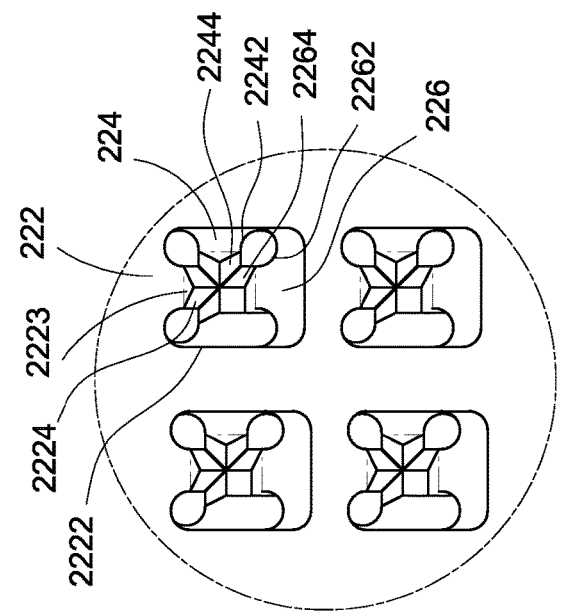
FIG. 7 is a top view of the microneedle set functioning as working electrode according to still another embodiment of the present invention.

FIG. 7 is a top view of the microneedle set functioning as working electrode according to still another embodiment of the present invention. The first microneedle set 22 comprises a first sheet 222, a second sheet 224, a third sheet 226 and a fourth sheet 228 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The fourth sheet 228 has at least one fourth through hole 2282 defined thereon, and a fourth barbule 2284 at peripheral of the fourth through hole 2282. The second barbule 2244, the third barbule 2264 and the fourth barbule 228 penetrates the first through hole 2222 to juxtapose the first barbule 2224, and the tips of the barbules are in rectangular arrangement from top view.

In the embodiments shown in FIGS. 4 to 7, the barbule 2224 of the first microneedle set 22 comprises a tip 2221 and a base 2223. The tips of those barbules, after the sheets are stacked together, are not at the same altitudes. Namely, some barbules pass more through holes than other barbules. Alternatively, the height of the barbules can be such designed, based on the stacked order of sheets, that the tips of those barbules, after the sheets are stacked together, are at the same altitudes.

Figure 8:
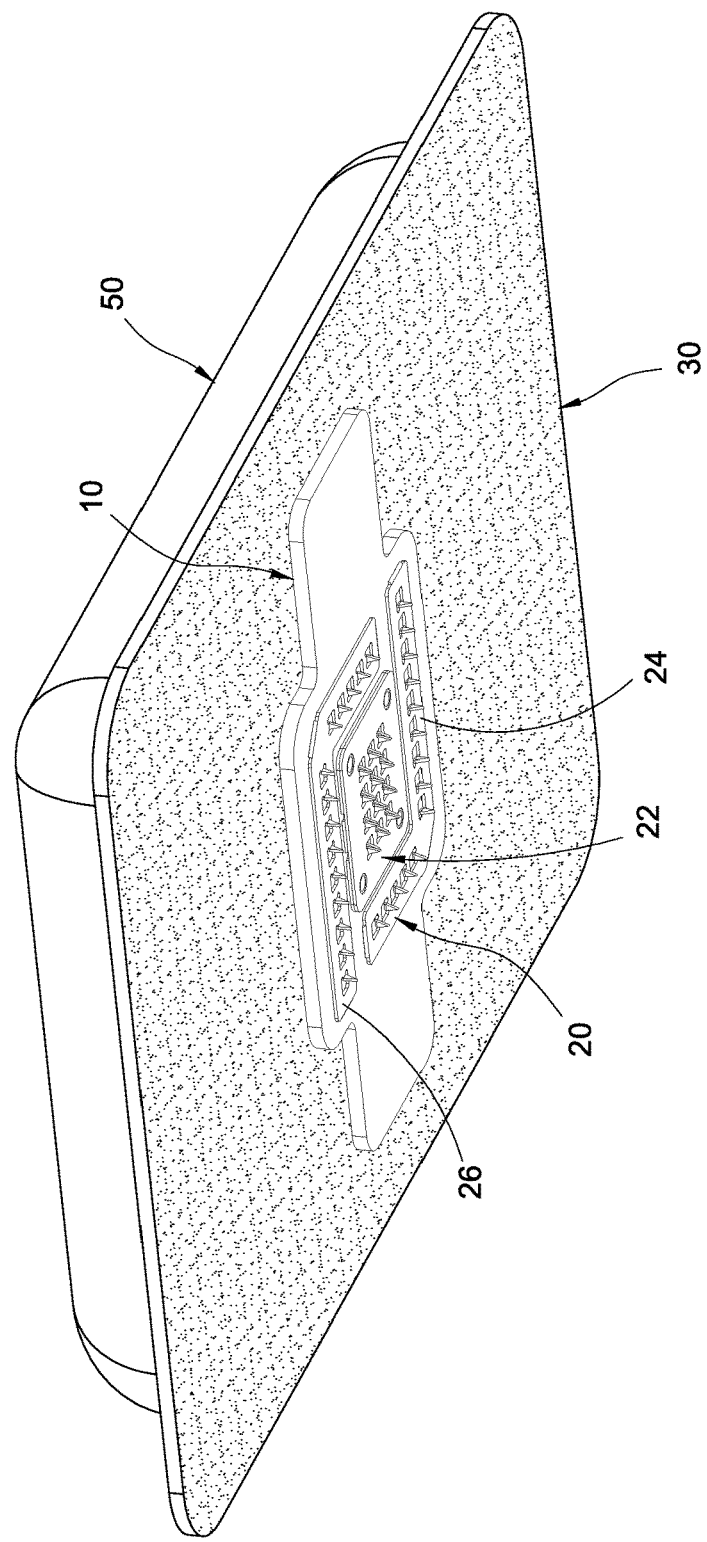
FIG. 8 shows a perspective of an assembled transdermal microneedles continuous monitoring system according to an embodiment of the present invention.
Figure 9:
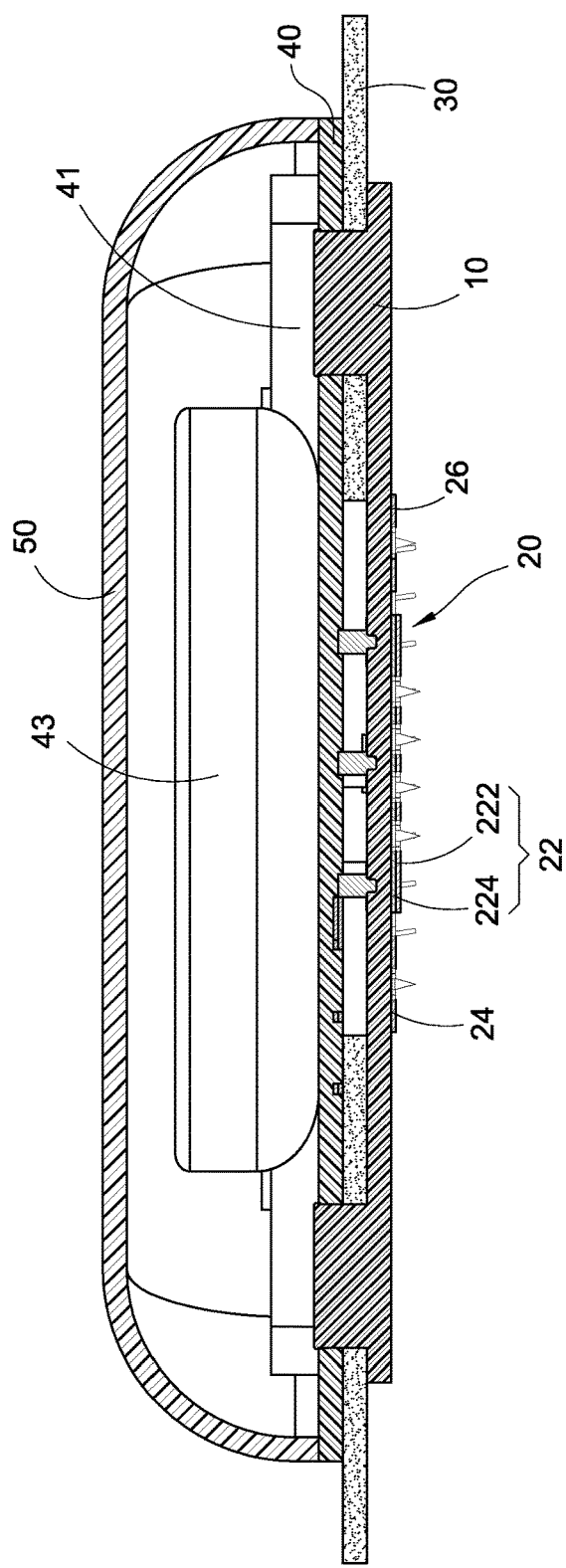
FIG. 9 shows a sectional of an assembled transdermal microneedles continuous monitoring system according to an embodiment of the present invention.

FIG. 8 shows a perspective of an assembled transdermal microneedles continuous monitoring system according to an embodiment of the present invention. FIG. 9 shows a sectional of an assembled transdermal microneedles continuous monitoring system according to an embodiment of the present invention. In this shown embodiment, the first microneedle set 22 comprises a first sheet 222 and a second sheet 224 stacked with each other. The first sheet 222 and the second sheet 224 can be assembled by punching peripherals thereof. The second microneedle set 24 comprises only a first sheet 242 and the third microneedle set 26 comprises only a first sheet 262. The transdermal microneedles continuous monitoring system of the present invention uses the flexible pad 30 to have tight fit with the user's muscle during operation thereof.

Figure 10:
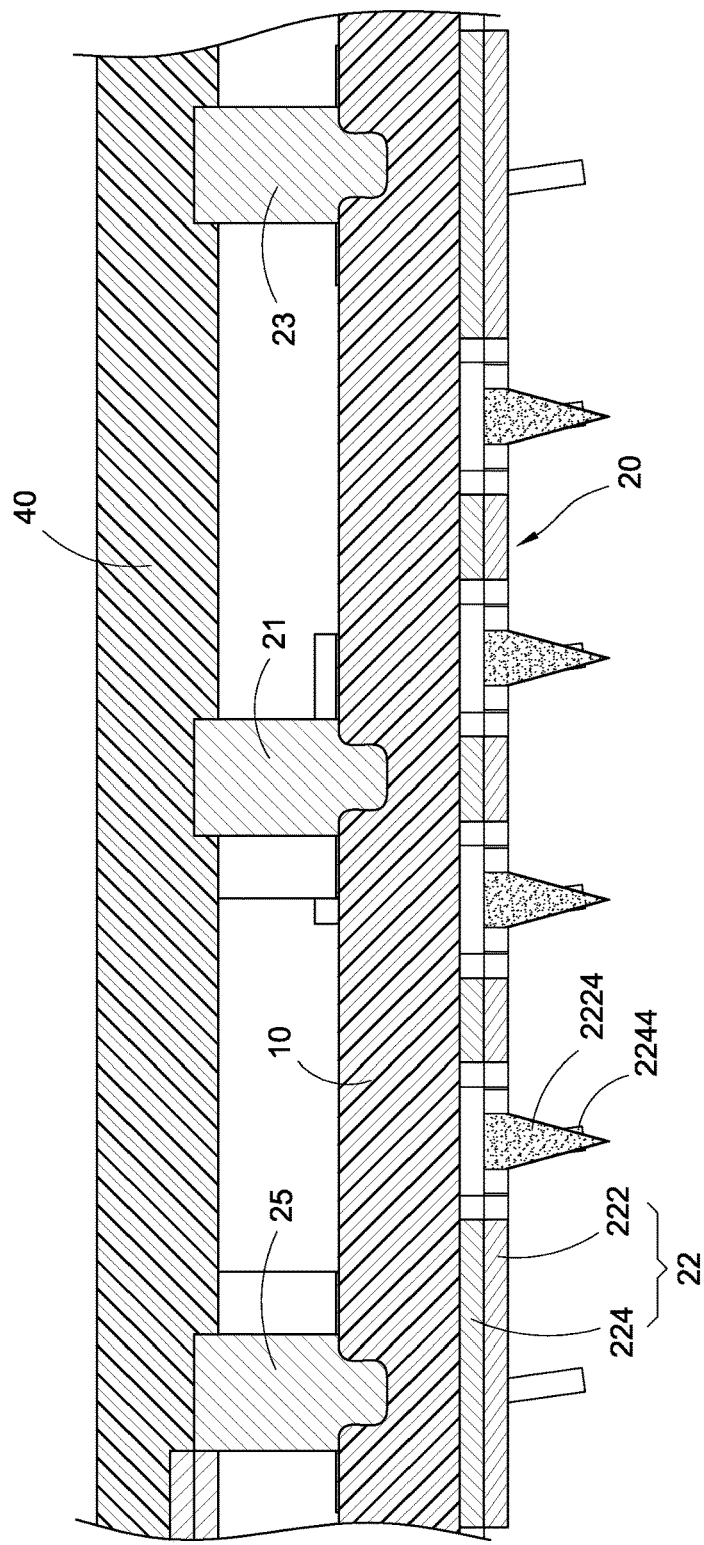
FIG. 10 is a partially sectional view of FIG. 9, where sensing polymer is coated on the barbules.

FIG. 10 is a partially sectional view of FIG. 9, where sensing polymer is coated on the barbules. More particularly, the sensing polymer is coated on the inner faces of the barbules, and anti-irritation medicine (medicine preventing skin from irritation) is coated on outer faces of the barbules. In this embodiment, the sensing polymer is a molecule selected from the group consisting of an antibody, an aptamer, a single-chain variable fragment (ScFv), a carbohydrate, glucose oxidase (GOx), hydroxybutyrate dehydrogenase (HBHD), and a combination thereof. The transdermal microneedles continuous monitoring system having barbules coated with the sensing polymer can sense the concentration data of hypodermal target molecules and determine the current physiological condition of user with the concentration data.

Figure 11:
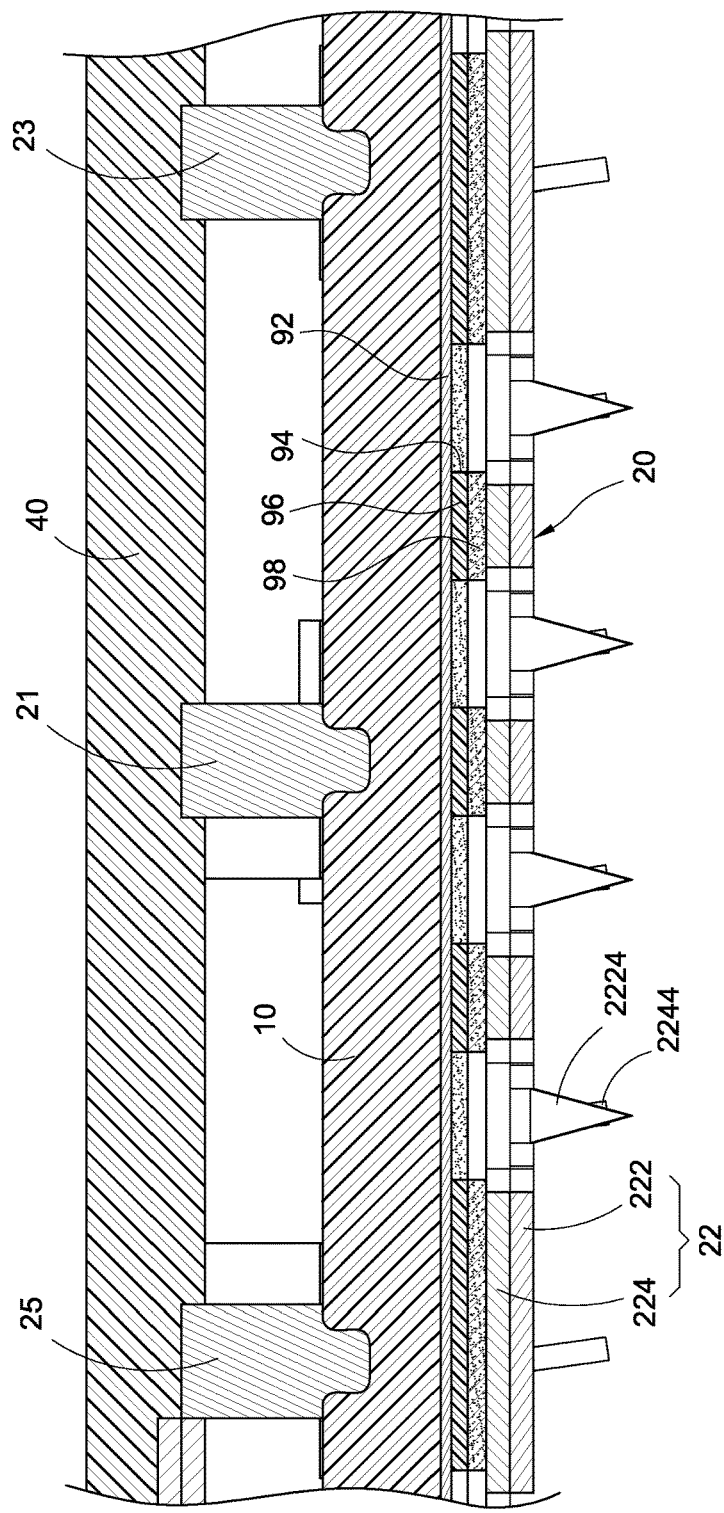
FIG. 11 is a partially sectional view of FIG. 9, where sensing polymer is coated on a test strip.

FIG. 11 is a partially sectional view of FIG. 9, where sensing polymer is coated on a test strip. The embodiment shown in this figure is different with the embodiment of FIG. 10 in that the first microneedle set 22 in this embodiment is used to withdraw interstitial fluid. Therefore, the sensing polymer is coated on a test strip below the first microneedle set 22 instead of coating on the barbules. In this embodiment, the test strip is arranged between the first microneedle set 22 and the substrate 10. The test strip comprises a conductive layer 92 and a plurality of test areas 94 on the conductive layer 92. The test areas 94 are coated with sensing polymer and aligned with the through holes 2222 of the first microneedle set 22. In this embodiment, the test areas 94 are defined by the resin plate 96. Moreover, the first microneedle set 22 is fixed to the test strip by a binding layer 98. In order to prevent the sensing polymer and the anti-irritation medicine from environment pollution, a protection layer such as an epoxy-polyurethane (Epoxy-PU) film is formed on the surface of the sensing polymer and the anti-irritation medicine.

Figure 12:
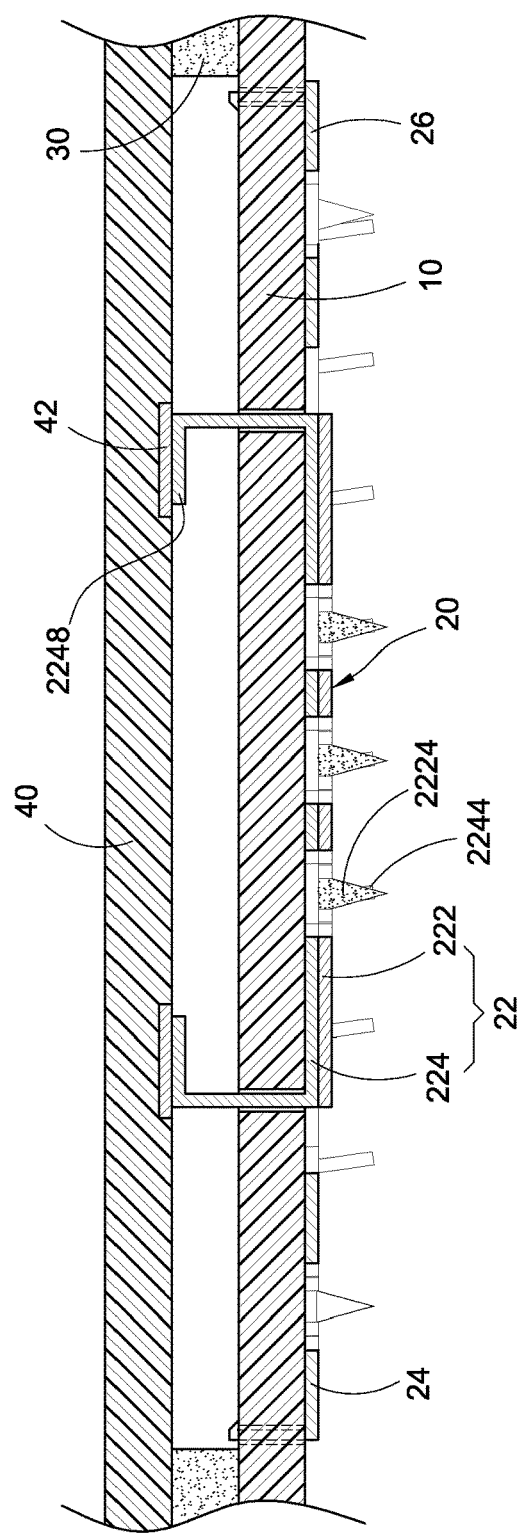
FIG. 12 shows a partially sectional view of an assembled transdermal microneedles continuous monitoring system according to another embodiment of the present invention.

FIG. 12 shows a partially sectional view of an assembled transdermal microneedles continuous monitoring system according to another embodiment of the present invention. In this embodiment, the conductive pin 2248 is bent to electrically connect the contact 42 on the circuit board 40, thus dispensing with the conductive post.

What is claimed is:

1. A transdermal microneedles continuous monitoring system, comprising:
   a substrate;
   a microneedle unit comprising at least a first microneedle set used as a working electrode and a second microneedle set used as a reference electrode, each of the microneedle sets comprising at least a microneedle, the first microneedle set comprising at least two sheets, each of the sheets having a through hole defined thereon and a barbule arranged at the peripheral of the through hole, the through hole on one sheet allowing the corresponding barbules of an other sheet to pass and the barbules being disposed separately;
   a signal processing unit arranged on the substrate and electrically connecting to the first microneedle set and the second microneedle set; and
   a power supply unit providing working power to the transdermal microneedles continuous monitoring system, wherein the at least two sheets comprise a first sheet and a second sheet stacked with the first sheet, the first sheet having at least one first through hole defined thereon, and a first barbule at the peripheral of the first through hole, the second sheet having at least one second through hole defined thereon and a second barbule at the peripheral of the second through hole, wherein the second barbule penetrates the first through hole to juxtapose the first barbule at a corresponding location.

2. The transdermal microneedles continuous monitoring system in claim 1, wherein each of the barbule of the first microneedle set comprises a tip and a base, wherein tips of the barbules are not at the same altitudes after the sheets are stacked and the through hole of one sheet are penetrated by the barbules of other sheets.

3. The transdermal microneedles continuous monitoring system in claim 1, wherein each of the barbule of the first microneedle set comprises a tip and a base, wherein the tips of the barbules are at the same altitudes after the sheets are stacked and the through hole of one sheet are penetrated by the barbules of other sheets.

4. The transdermal microneedles continuous monitoring system in claim 1, wherein the microneedles of first microneedle set and the second microneedle set are formed by punching or etching.

5. The transdermal microneedles continuous monitoring system in claim 1, wherein each the barbules has sensing polymer coated on inner surface thereof.

6. The transdermal microneedles continuous monitoring system in claim 1, wherein each the barbules has anti-irritation medicine coated on outer surface thereof.

7. The transdermal microneedles continuous monitoring system in claim 1, further comprising a test strip arranged between the first microneedle set and the substrate, the test strip comprises a conductive layer and a plurality of test areas on the conductive layer, the test areas are coated with sensing polymer and aligned with the through holes of the first microneedle set.

8. The transdermal microneedles continuous monitoring system in claim 5, further comprising a protection layer on the sensing polymer.

9. The transdermal microneedles continuous monitoring system in claim 6, further comprising a protection layer on the anti-irritation medicine.

10. The transdermal microneedles continuous monitoring system in claim 1, wherein the material of the barbules is selected from the group consisting of stainless steel, nickel, nickel alloy, titanium, titanium alloy, carbon nanotube, and silicon, the surface of the barbules is coated with biologically compatible metal.

11. The transdermal microneedles continuous monitoring system in claim 1, wherein the material of the barbules is resin, the surface of the barbules is coated with biologically compatible metal.

* * * * *